(12) United States Patent
Himmelsbach

(10) Patent No.: US 8,372,855 B2
(45) Date of Patent: Feb. 12, 2013

(54) CYCLOHEXYLOXY-SUBSTITUTED HETEROCYCLICS, MEDICINES CONTAINING THESE COMPOUNDS AND METHOD FOR THE PRODUCTION THEREOF

(75) Inventor: Frank Himmelsbach, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/057,874

(22) PCT Filed: Jul. 23, 2009

(86) PCT No.: PCT/EP2009/059511
§ 371 (c)(1),
(2), (4) Date: Mar. 24, 2011

(87) PCT Pub. No.: WO2010/015523
PCT Pub. Date: Feb. 11, 2010

(65) Prior Publication Data
US 2012/0115825 A1 May 10, 2012

(30) Foreign Application Priority Data
Aug. 8, 2008 (EP) .................................. 08104994

(51) Int. Cl.
*A01N 43/54* (2006.01)
*A61K 31/517* (2006.01)
*C07D 239/72* (2006.01)

(52) U.S. Cl. ................. 514/266.1; 544/283; 544/287
(58) Field of Classification Search .............. 544/283, 544/287; 514/266.1
See application file for complete search history.

(56) References Cited

FOREIGN PATENT DOCUMENTS

| CA | 2476008 A1 | 10/2003 |
|---|---|---|
| CA | 2669187 A1 | 5/2008 |
| WO | 03082290 A1 | 10/2003 |
| WO | WO03/082290 | * 10/2003 |
| WO | 2008055854 A1 | 5/2008 |
| WO | WO 2008/055854 | * 5/2008 |

OTHER PUBLICATIONS

McMahon et al.*
Pinedo et al.*
McMahon et al (2000).*
Pinedo et al (2000).*
International Search Report dated Sep. 18, 2009, corresponding to PCT Application No. PCT/EP2009/059511.

* cited by examiner

*Primary Examiner* — Paul V. Ward
(74) *Attorney, Agent, or Firm* — Michael P. Morris; Edward S. Lazer

(57) ABSTRACT

The present invention relates to cyclohexyloxy-substituted heterocycles of general formula (I)

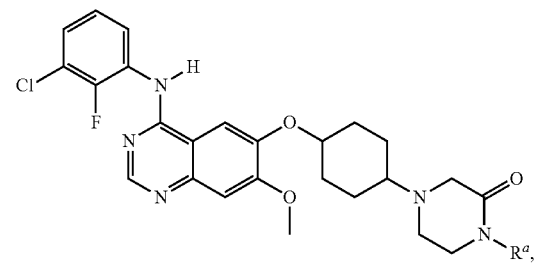

(I)

the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways and the preparation thereof.

4 Claims, No Drawings

CYCLOHEXYLOXY-SUBSTITUTED HETEROCYCLICS, MEDICINES CONTAINING THESE COMPOUNDS AND METHOD FOR THE PRODUCTION THEREOF

The present invention relates to cyclohexyloxy-substituted heterocycles of general formula

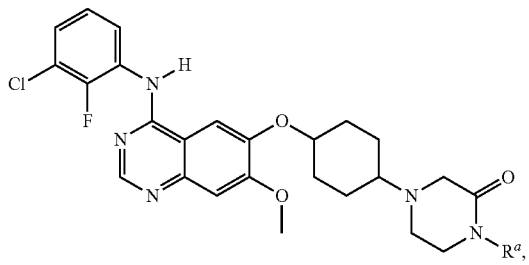

(I)

the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways and the preparation thereof.

The problem of the present invention is to prepare new compounds which on the basis of their pharmaceutical effectiveness as tyrosine-kinase inhibitors, may be used therapeutically, i.e. for the treatment of pathophysiological processes caused by hyperfunction of tyrosine kinases.

DETAILED DESCRIPTION OF THE INVENTION

It has surprisingly been found that the problem mentioned above is solved by compounds of formula (I), wherein the group $R^a$ has the meanings given hereinafter.

The present invention therefore relates to compounds of general formula (I),

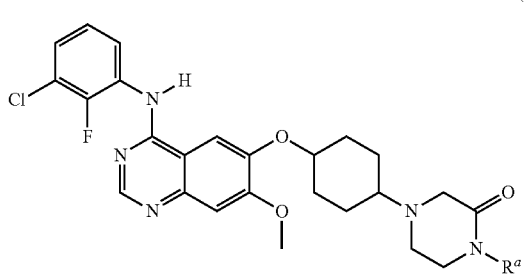

(I)

wherein
$R^a$ denotes an ethyl, propyl, butyl, cyclopropyl, cyclopropylmethyl, cyclobutyl, cyclobutylmethyl, 3-tetrahydrofuranyl, tetrahydrofuranylmethyl, 3-tetrahydropyranyl, 4-tetrahydropyranyl and tetrahydropyranylmethyl group, and wherein, unless stated otherwise, the above-mentioned alkyl groups may be straight-chain or branched, optionally in the form of the tautomers, the racemates, the enantiomers, the diastereomers and the mixtures thereof, and optionally the pharmacologically acceptable acid addition salts thereof, and the solvates and hydrates thereof.

Preferred compounds of formula (I) are those wherein $R^a$ denotes a group selected from among ethyl, butyl, cyclopropylmethyl and 4-tetrahydropyranyl group,
optionally in the form of the tautomers, the racemates, the enantiomers, the diastereomers and the mixtures thereof, and optionally the pharmacologically acceptable acid addition salts thereof, the solvates and hydrates thereof.

The invention also relates to compounds of formula (I) for use as medicaments. Preferably the compounds of formula (I) are used in cases of inflammatory or allergic diseases of the airways.

The compounds of formula (I) are particularly preferably used in cases of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, e.g. radiation-induced or caused by aspiration or infectious pneumonitis, collagenoses such as lupus erythematodes, systemic sclerodermy, sarcoidosis and Boeck's disease.

It is also particularly preferred to use the compounds of formula (I) in cases of inflammatory or allergic complaints in which autoimmune reactions are involved. It is also particularly preferred to use the compounds of formula (I) in cases of a disease in the form of benign or malignant tumours.

The invention further relates to a pharmaceutical formulation containing a compound of formula (I).

Preferably an orally administered pharmaceutical formulation containing a compound of formula (I) is used.

The invention further relates to medicament combinations which contain, besides one or more compounds of formula (I), as further active substances, one or more compounds selected from among the categories of betamimetics, anticholinergics, corticosteroids, further PDE4-inhibitors, LTD4-antagonists, EGFR-inhibitors, dopamine agonists, H1-antihistamines, PAF-antagonists and PI3-kinase inhibitors or double or triple combinations thereof.

Examples of betamimetics which may be used here preferably include compounds which are selected from among arformoterol, carmoterol, formoterol, indacaterol, salmeterol, albuterol, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramid, tolubuterol, zinterol and 6-hydroxy-8-{1-hydroxy-2-[2-(4-methoxy-phenyl)-1,1-dimethyl-ethylamino]-ethyl}-4H-benzo[1,4]oxazin-3-one 8-{2-[2-(2,4-difluoro-phenyl)-1,1-dimethyl-ethylamino]-1-hydroxy-ethyl}-6-hydroxy-4H-benzo[1,4]oxazin-3-one 8-{2-[2-(3,5-difluoro-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 8-{2-[2-(4-fluoro-phenyl)-1,1-dimethyl-ethylamino]-1-hydroxy-ethyl}-6-hydroxy-4H-benzo[1,4]oxazin-3-one N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide 8-{2-[1,1-dimethyl-3-(2-oxo-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(6-methyl-2-oxo-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(2-oxo-5-trifluoromethyl-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(3-methyl-2-oxo-2,3-dihydro-benzoimidazol-1-yl)-propylamino]-1-hydroxy-ethyl}-6-hydroxy-4H-benzo[1,4]oxazin-3-one N-[2-hydroxy-5-((1R)-1-hydroxy-2-{2-[4-(2-hydroxy-2-phenyl-ethylamino)-phenyl]-ethylamino}-ethyl)-phenyl]-formamide 8-hydroxy-5-((1R)-1-hydroxy-2-{2-[4-(6-methoxy-biphenyl-3-ylamino)-phenyl]-ethylamino}-ethyl)-1H-quinolin-2-one 8-hydroxy-5-[(1R)-1-hydroxy-2-(6-phenethylamino-hexylamino)-ethyl]-1H-quinolin-2-one 5-[(1R)-2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[(2R)-2-hydroxy-2-(4-hydroxy-3-hydroxymethyl-phenyl)-ethylamino]-hexyloxy}-butyl)-5-methyl-phenyl]-urea 4-((1R)-2-{6-[2-(2,6-dichloro-benzyloxy)-ethoxy]-hexylamino}-1-hydroxy-ethyl)-2-hydroxymethyl-phenol 3-(4-{6-[(2R)-2-hydroxy-2-(4-hydroxy-3-hydroxymethyl-phenyl)-ethylamino]-hexyloxy}-butyl)-benzenesulphonamide 3-(3-{7-[(2R)-2-hydroxy-2-(4-hydroxy-3-hydroxymethyl-phenyl)-ethylamino]-heptyloxy}-propyl)-benzenesulphonamide 4-((1R)-2-{6-[4-(3-cyclopentanesulphonyl-phenyl)-butoxy]-hexylamino}-1-hydroxy-ethyl)-2-hydroxymethyl-phenol N-1-adamantanyl-2-{3-[(2R)-2-({(2R)-2-hydroxy-2-[4-hydroxy-3-(hydroxymethyl)phenyl]ethyl}amino)propyl]phenyl}acetamide (1R)-5-{2-[6-(2,2-difluoro-2-phenyl-ethoxy)-hexylamino]-1-hydroxy-ethyl}-8-hydroxy-1H-quinolin-2-one (R,S)-4-(2-{[6-(2,2-difluoro-4-phenylbutoxy)hexyl]amino}-1-hydroxy-ethyl)-2-(hydroxymethyl)phenol (R,S)-4-(2-{[6-(2,2-difluoro-2-phenylethoxy)hexyl]amino}-1-hydroxy-ethyl)-2-(hydroxymethyl)phenol (R,S)-4-(2-{[4,4-difluoro-6-(4-phenylbutoxy)hexyl]amino}-1-hydroxy-ethyl)-2-(hydroxymethyl)phenol (R,S)-4-(2-{[6-(4,4-difluoro-4-phenylbutoxy)hexyl]amino}-1-hydroxy-ethyl)-2-(hydroxymethyl)phenol (R,S)-5-(2-{[6-(2,2-difluoro-2-phenylethoxy)hexyl]amino}-1-hydroxy-ethyl)-8-hydroxyquinolin-2(1H)-one (R,S)-[2-({6-[2,2-difluoro-2-(3-methylphenyl)ethoxy]hexyl}amino)-1-hydroxyethyl]-2-(hydroxymethyl)phenol 4-(1R)-2-{[6-(2,2-difluoro-2-phenylethoxy)hexyl]amino}-1-hydroxyethyl)-2-(hydroxymethyl)phenol (R,S)-2-(hydroxymethyl)-4-(1-hydroxy-2-{[4,4,5l5-tetrafluoro-6-(3-phenylpropoxy)-hexyl]amino}ethyl)phenol (R,S)-[5-(2-{[6-(2,2-difluoro-2-phenylethoxy)hexyl]amino}-1-hydroxy-ethyl)-2-hydroxyphenyl]formamide (R,S)-4-[2-({6-[2-(3-bromophenyl)-2,2-difluoroethoxy]hexyl}amino)-1-hydroxyethyl]-2-(hydroxymethyl)phenol (R,S)—N-[3-(1,1-difluoro-2-{[6-({2-hydroxy-2-[4-hydroxy-3-(hydroxymethyl)phenyl]-ethyl}amino)hexyl]oxy}ethyl)phenyl]-urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidin-2,4-dione (R,S)-4-[2-({6-[2,2-difluoro-2-(3-methoxyphenyl)ethoxy]hexyl}amino)-1-hydroxyethyl]-2-(hydroxymethyl)phenol 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-difluoro-6-(4-phenylbutoxy)hexyl]amino}-1-hydroxy-ethyl)-2-(hydroxymethyl)phenol (R,S)-4-(2-{[6-(3,3-difluoro-3-phenylpropoxy)hexyl]amino}-1-hydroxy-ethyl)-2-(hydroxymethyl)phenol (R,S)-(2-{[6-(2,2-difluoro-2-phenylethoxy)hexyl]amino}-1-hydroxy-ethyl)-2-(hydroxymethyl)phenol (R,S)-4-(2-{[6-(2,2-difluoro-3-phenylpropoxy)hexyl]amino}-1-hydroxy ethyl)-2-(hydroxymethyl)phenol 3-[2-(3-chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide N-(2-diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide 7-[2-(2-{3-[2-(2-chloro-phenyl)-ethylamino]-propylsulphanyl}-ethylamino)-1-hydroxy-ethyl]-4-hydroxy-3H-benzothiazol-2-one optionally in the form of the racemates, enantiomers, diastereomers and optionally in the form of the pharmacologically acceptable acid addition salts, solvates or hydrates thereof. Preferably, according to the invention, the acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of anticholinergics which may be used here preferably include compounds which are selected from among: tiotropium salts, preferably the bromide salt, oxitropium salts, preferably the bromide salt, flutropium salts, preferably the bromide salt, ipratropium salts, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthen-9-carbonyloxy)-1-azoniabicyclo[2,2,2]octane-salts. In the above-mentioned salts the cations are the pharmacologically active constituents. As $X^-$ anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are:
tropenol 2,2-diphenylpropionate methobromide,
scopine 2,2-diphenylpropionate methobromide, scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide,
tropenol 9-fluoro-fluorene-9-carboxylate methobromide,
scopine 9-hydroxy-fluorene-9-carboxylate methobromide,
scopine 9-fluoro-fluorene-9-carboxylate methobromide;
tropenol 9-methyl-fluorene-9-carboxylate methobromide,
scopine 9-methyl-fluorene-9-carboxylate methobromide,
cyclopropyltropine benzilate methobromide,
cyclopropyltropine 2,2-diphenylpropionate methobromide,
cyclopropyltropine 9-hydroxy-xanthene-9-carboxylate methobromide,
cyclopropyltropine 9-methyl-fluorene-9-carboxylate methobromide,
cyclopropyltropine 9-methyl-xanthene-9-carboxylate methobromide,
cyclopropyltropine 9-hydroxy-fluorene-9-carboxylate methobromide,
cyclopropyltropine methyl 4,4'-difluorobenzilate methobromide,
tropenol 9-hydroxy-xanthene-9-carboxylate methobromide,
scopine 9-hydroxy-xanthene-9-carboxylate methobromide,
tropenol 9-methyl-xanthene-9-carboxylate-methobromide,
scopine 9-methyl-xanthene-9-carboxylate-methobromide,
tropenol 9-ethyl-xanthene-9-carboxylate methobromide,
tropenol 9-difluoromethyl-xanthene-9-carboxylate methobromide,
scopine 9-hydroxymethyl-xanthene-9-carboxylate methobromide.

The above-mentioned compounds may also be used as salts within the scope of the present invention, while instead of the methobromide, the metho-X salts may be used wherein X may have the meanings given hereinbefore for X⁻.

Compounds which may be used as corticosteroids are preferably those selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, tipredane and
pregna-1,4-diene-3,20-dione, 6-fluoro-1-hydroxy-16,17-[(1-methylethylidene)bis(oxy)]-21-[[4-[(nitrooxy)methyl]benzoyl]oxy]-, (6-alpha,11-beta,16-alpha)-(9Cl) (NCX-1024),
16,17-butylidenedioxy-6,9-difluoro-11-hydroxy-17-(methylthio)androst-4-en-3-one (RPR-106541),
(S)-fluoromethyl 6,9-difluoro-17-[(2-furanylcarbonyl)oxy]-11-hydroxy-16-methyl-3-oxo-androsta-1,4-diene-17-carbothionate,
(S)-(2-oxo-tetrahydro-furan-3S-yl) 6,9-difluoro-11-hydroxy-16-methyl-3-oxo-17-propionyloxy-androsta-1,4-dien-17-carbothionate,
cyanomethyl 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylate,
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, apremilast, arofyllin, atizoram, oglemilastum, tetomilast, and
5-[(N-(2,5-dichloro-3-pyridinyl)-carboxamide]-8-methoxy-quinoline (D-4418),
N-(3,5-dichloro-1-oxido-4-pyridinyl)-carboxamide]-8-methoxy-2-(trifluoromethyl)-quinoline (D-4396 (Sch-351591)), N-(3,5-dichloropyrid-4-yl)-[1-(4-fluorobenzyl)-5-hydroxy-indol-3-yl]glyoxylic acid amide (AWD-12-281 (GW-842470)), 9-[(2-fluorophenyl)methyl]-N-methyl-2-(trifluoromethyl)-9H-purin-6-amine (NCS-613),
4-[(2R)-2-[3-(cyclopentyloxy)-4-methoxyphenyl]-2-phenylethyl]-pyridine (CDP-840),
N-[(3R)-3,4,6,7-tetrahydro-9-methyl-4-oxo-1-phenylpyrrolo[3,2,1-jk][1,4]benzodiazepin-3-yl]-4-pyridinecarboxamide (PD-168787),
4-[6,7-diethoxy-2,3-bis(hydroxymethyl)-1-naphthalenyl]-1-(2-methoxyethyl)-2(1H)-pyridinone (T-440),
2-[4-[6,7-diethoxy-2,3-bis(hydroxymethyl)-1-naphthalenyl]-2-pyridinyl]-4-(3-pyridinyl)-1(2H)-phthalazinone (T-2585),
(3-(3-cyclopenyloxy-4-methoxybenzyl)-6-ethylamino-8-isopropyl-3H-purine (V-11294A),
beta-[3-(cyclopentyloxy)-4-methoxyphenyl]-1,3-dihydro-1,3-dioxo-2H-isoindole-2-propanamide (CDC-801),
imidazo[1,5-a]pyrido[3,2-e]pyrazin-6(5H)-one, 9-ethyl-2-methoxy-7-methyl-5-propyl-(D-22888),
5-[3-(cyclopentyloxy)-4-methoxyphenyl]-3-[(3-methylphenyl)methyl], (3S,5S)-2-piperidinone (HT-0712),
4-[1-[3,4-bis(difluoromethoxy)phenyl]-2-(3-methyl-1-oxido-4-pyridinylethyl]-alpha,alpha-bis(trifluoromethyl)-benzenemethanol (L-826141),
N-(3,5-dichloro-1-oxo-pyridin-4-yl)-4-difluoromethoxy-3-cyclopropylmethoxybenzamide,
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide,
(R)-(+)-1-(4-bromobenzyl)-4-[(3-cyclopentyloxy)-4-methoxyphenyl]-2-pyrrolidone,
3-(cyclopentyloxy-4-methoxyphenyl)-1-(4-N'-[N-2-cyano-5-methyl-isothioureido]benzyl)-2-pyrrolidone,
cis[4-cyano-4-(3-cyclopentyloxy-4-methoxyphenyl)cyclohexane-1-carboxylic acid],
2-carbomethoxy-4-cyano-4-(3-cyclopropylmethoxy-4-difluoromethoxyphenyl)cyclohexan-1-one,
cis[4-cyano-4-(3-cyclopropylmethoxy-4-difluoromethoxyphenyl)cyclohexan-1-ol],
(R)-(+)-ethyl[4-(3-cyclopentyloxy-4-methoxyphenyl)pyrrolidin-2-ylidene]acetate,
(S)-(−)-ethyl[4-(3-cyclopentyloxy-4-methoxyphenyl)pyrrolidin-2-ylidene]acetate,
9-cyclopentyl-5,6-dihydro-7-ethyl-3-(2-thienyl)-9H-pyrazolo[3,4-c]-1,2,4-triazolo[4,3-a]pyridine,
9-cyclopentyl-5,6-dihydro-7-ethyl-3-(tert-butyl)-9H-pyrazolo[3,4-c]-1,2,4-triazolo[4,3-a]pyridine,
optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

EGFR inhibitors which may be used are preferably compounds selected from among cetuximab, trastuzumab, panitumumab (=ABX-EGF), Mab ICR-62, gefitinib, canertinib, erlotinib, and 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline,
4-[(3-chloro-4-fluoro-phenyl)amino]-6-(tetrahydropyran-4-yloxy)-7-(2-acetylamino-ethoxy)-quinazoline,
4-[(3-chloro-4-fluoro-phenyl)amino]-6-(tetrahydropyran-4-yloxy)-7-(2-methanesulphonylamino-ethoxy)-quinazoline,
4-[(3-chloro-4-fluoro-phenyl)amino]-6-{1-[(piperidin-1-yl)carbonyl]-piperidin-4-yloxy}-7-methoxy-quinazoline,
4-[(3-chloro-4-fluoro-phenyl)amino]-6-(1-aminocarbonylmethyl-piperidin-4-yloxy)-7-methoxy-quinazoline,
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline,
4-[(3-chloro-4-fluoro-phenyl)amino]-6-(trans-4-ethansulphonylamino-cyclohexan-1-yloxy)-7-methoxy-quinazoline,
4-[(3-chloro-4-fluoro-phenyl)amino]-6-(1-methanesulphonyl-piperidin-4-yloxy)-7-ethoxy-quinazoline,
4-[(3-chloro-4-fluoro-phenyl)amino]-6-(1-methanesulphonyl-piperidin-4-yloxy)-7-(2-methoxy-ethoxy)-quinazoline,
4-[(3-chloro-4-fluoro-phenyl)amino]-6-[1-(2-methoxy-acetyl)-piperidin-4-yloxy]-7-(2-methoxy-ethoxy)-quinazoline,
4-[(3-chloro-4-fluoro-phenyl)amino]-6-(cis-4-acetylamino-cyclohexan-1-yloxy)-7-methoxy-quinazoline,
4-[(3-ethynyl-phenyl)amino]-6-[1-(tert.-butyloxycarbonyl)-piperidin-4-yloxy]-7-methoxy-quinazoline,
4-[(3-ethynyl-phenyl)amino]-6-(tetrahydropyran-4-yloxy]-7-methoxy-quinazoline,
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline,
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline,
4-[(3-chloro-4-fluoro-phenyl)amino]-6-{cis-4-[(morpholin-4-yl)carbonylamino]-cyclohexan-1-yloxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-chloro-4-fluoro-phenyl)amino]-6-{1-[(morpholin-4-yl)carbonyl]-piperidin-4-yloxy}-7-(2-methoxy-ethoxy)-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-chloro-4-fluoro-phenyl)amino]-6-(1-methyl-piperidin-4-yloxy)-7(2-methoxy-ethoxy)-quinazoline,
4-[(3-chloro-4-fluoro-phenyl)amino]-6-(1-isopropyloxycarbonyl-piperidin-4-yloxy)-7-methoxy-quinazoline,
4-[(3-chloro-4-fluoro-phenyl)amino]-6-(cis-4-methylamino-cyclohexan-1-yloxy)-7-methoxy-quinazoline,
4-[(3-chloro-4-fluoro-phenyl)amino]-6-{cis-4-[N-(2-methoxy-acetyl)-N-methyl-amino]-cyclohexan-1-yloxy}-7-methoxy-quinazoline,
4-[(3-ethynyl-phenyl)amino]-6-(piperidin-4-yloxy)-7-methoxy-quinazoline,
4-[(3-ethynyl-phenyl)amino]-6-[1-(2-methoxy-acetyl)-piperidin-4-yloxy]-7-methoxy-quinazoline,
4-[(3-ethynyl-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(cis-2,6-dimethyl-morpholin-4-yl)carbonyl]-piperidin-4-yloxy}-7-methoxy-quinazoline,
4-[(3-chloro-4-fluoro-phenyl)amino]-6-{1-[(2-methyl-morpholin-4-yl)carbonyl]-piperidin-4-yloxy}-7-methoxy-quinazoline,
4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline,
4-[(3-chloro-4-fluoro-phenyl)amino]-6-{1-[(N-methyl-N-2-methoxyethyl-amino)carbonyl]-piperidin-4-yloxy}-7-methoxy-quinazoline,
4-[(3-chloro-4-fluoro-phenyl)amino]-6-(1-ethyl-piperidin-4-yloxy)-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-{1-[(3-methoxypropyl-amino)-carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexan-1-yloxy]-7-methoxy-quinazoline,
4-[(3-chloro-4-fluoro-phenyl)amino]-6-[cis-4-(N-acetyl-N-methyl-amino)-cyclohexan-1-yloxy]-7-methoxy-quinazoline,
4-[(3-chloro-4-fluoro-phenyl)amino]-6-(trans-4-methylamino-cyclohexan-1-yloxy)-7-methoxy-quinazoline,
4-[(3-chloro-4-fluoro-phenyl)amino]-6-[trans-4-(N-methanesulphonyl-N-methyl-amino)-cyclohexan-1-yloxy]-7-methoxy-quinazoline,
4-[(3-chloro-4-fluoro-phenyl)amino]-6-(trans-4-dimethylamino-cyclohexan-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline,
4-[(3-chloro-4-fluoro-phenyl)amino]-6-(1-cyano-piperidin-4-yloxy)-7-methoxy-quinazoline,
3-cyano-4-[(3-chloro-4-fluorophenyl)amino]-6-{[4-(N,N-dimethylamino)-1-oxo-2-buten-1-yl]amino}-7-ethoxy-quinoline;
[4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline,
4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline,
4-[(3-chloro-4-fluoro-phenyl)amino]-7-[2-((S)-6-methyl-2-oxo-morpholin-4-yl)-ethoxy]-6-[(vinylcarbonyl)amino]-quinazoline,
4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, and 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxyquinazoline, optionally in the form of the racemates, enantiomers or diastereomers thereof and optionally in the form of the pharmacologically acceptable acid addition salts, solvates and/or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used here are preferably compounds selected from among montelukast, pranlukast, zafirlukast, and (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio)propoxy]-2-propylphenoxy]butyric acid (MN-001), 1-(((R)-(3-(2-(6,7-difluoro-2-quinolinyl)ethenyl)phenyl)-3-(2-(2-hydroxy-2-propyl)phenyl)thio)methylcyclopropaneacetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)

cyclopropaneacetic acid, [2-[[2-(4-tert-butyl-2-thiazolyl)-5-benzofuranyl]oxymethyl]phenyl]acetic acid optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-receptor antagonists are optionally capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Histamine H1 receptor antagonists which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, olopatadine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of PAF-antagonists preferably include compounds selected from among lexipafant and 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinylcarbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. Preferred acid addition salts according to the invention are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine receptor agonists used are preferably compounds selected from among bromocriptine, cabergoline, alpha-dihydroergocryptine, lisuride, pergolide, pramipexole, roxindole, ropinirole, talipexole, terguride and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of substances of preferred PI3 kinase antagonists that may be used are preferably compounds selected from among 5-(quinoxalin-6-ylmethylene)thiazolidine-2,4-dione (AS-605240), 2-[(6-amino-9H-purin-9-yl)methyl]-5-methyl-3-(2-methylphenyl)-4(3H)-quinazolinone (C-87114), 2-methyl-2-[4-[3-methyl-2-oxo-8-(quinoline-3-yl)-2,3-dihydroimidazo[4,5-c]quinolin-1-yl]phenyl]propionitrile (BEZ-235), optionally in the form of the racemates, enantiomers, diastereomers thereof and optionally in the form of the pharmacologically acceptable acid addition salts, prodrugs, solvates or hydrates thereof.

TERMS AND DEFINITIONS USED

By the term "optionally substituted" is meant within the scope of the invention the above-mentioned group, optionally substituted by a lower-molecular group. Examples of lower-molecular groups regarded as chemically meaningful are groups consisting of 1-25 atoms.

Preferably such groups have no negative effect on the pharmacological efficacy of the compounds.

For example the groups may comprise:
Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

Also included in the subject-matter of this invention are the compounds according to the invention, including the salts thereof, wherein one or more hydrogen atoms, for example one, two, three, four or five hydrogen atoms, are replaced by deuterium.

Where a hyphen open on one side "-" is used in the structural formula of a substituent, this hyphen is to be understood as the linkage point to the remainder of the molecule. The substituent replaces the corresponding groups $R^a$, $R^b$, etc. If no hyphen open on one side is used in the structural formula of a substituent, the linkage point to the remainder of the molecule is clear from the structural formula itself.

Compounds of general formula (I) may contain acid groups, primarily carboxyl groups, and/or basic groups such as e.g. amino functions. Compounds of general formula (I) may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali metal or alkaline earth metal hydroxides or carbonates, zinc or ammonium hydroxides or organic amines such as e.g. diethylamine, triethylamine, triethanolamine, inter alia. For preparing the alkali metal and alkaline earth metal salts of the compound of formula (I), it is preferable to use the alkali metal and alkaline earth metal hydroxides and hydrides, while the hydroxides and hydrides of the alkali metals, particularly sodium and potassium are preferred, and sodium and potassium hydroxide are particularly preferred. (See also Pharmaceutical Salts, S. M. Birge et al., *J. Pharm. Sci.* (1977), 66, 1-19)

As already mentioned, the compounds of general formula (I) may be converted into the salts thereof, particularly for pharmaceutical use, into the pharmacologically acceptable acid addition salts thereof with an inorganic or organic acid. Suitable acids for this purpose include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. In addition, mixtures of the above-mentioned acids may be used.

The present invention relates to the respective compounds, optionally in the form of the individual diastereomers, mixtures of the individual diastereomers and/or individual enantiomers, mixtures of the individual enantiomers or racemates thereof, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example tartaric acid, fumaric acid, citric acid or methanesulphonic acid.

"Protective groups" for the purposes of the present invention is a collective term for organic groups with which certain functional groups of a molecule containing a number of active centres can temporarily be protected from attack by reagents so that reactions take place only at the desired (unprotected) sites. The protective groups should be introduced selectively under mild conditions. They must be stable for the duration of the protection under all the conditions of the reactions and purifying procedures which are to be carried out; racemisations and epimerisations must be suppressed. Protective groups should be capable of being cleaved again under mild conditions selectively and ideally in high yields. The choice of a suitable protective group, the reaction conditions (solvent, temperature, duration, etc.), and also the options for removing a protective group are known in the art (e.g. Philip Kocienski, Protecting Groups, 3rd ed. 2004, THIEME, Stuttgart, ISBN: 3131370033).

By an "organic solvent" is meant, within the scope of the invention, an organic, low-molecular substance which can dissolve other organic substances by a physical method. To be suitable the prerequisite for the solvent is that neither the dissolving substance nor the dissolved substance should be chemically altered during the dissolving process, i.e. the components of the solution should be recoverable in their original form by physical separation processes such as distillation, crystallisation, sublimation, evaporation or adsorption. For various reasons, not only the pure solvents but also mixtures that combine the dissolving properties may be used. Examples include:

alcohols, preferably methanol, ethanol, propanol, butanol, octanol, cyclohexanol;
glycols, preferably ethyleneglycol, diethyleneglycol;
ethers/glycolethers, preferably diethyl ether, tert-butylmethylether, dibutylether, anisole, dioxane, tetrahydrofuran, mono-, di-, tri-, polyethyleneglycol ethers;
ketones, preferably acetone, butanone, cyclohexanone;
esters, preferably acetic acid esters, glycolesters;
amides and other nitrogen compounds, preferably dimethylformamide, pyridine, N-methylpyrrolidone, acetonitrile;
sulphur compounds, preferably carbon disulphide, dimethylsulphoxide, sulpholane;
nitro compounds, preferably nitrobenzene;
halogenated hydrocarbons, preferably dichloromethane, chloroform, tetrachlormethane, tri- and tetrachloroethene, 1,2-dichloroethane, chlorofluorocarbons;
aliphatic or alicyclic hydrocarbons, preferably benzines, petroleum ether, cyclohexane, methylcyclohexane, decaline, terpene-L; or
aromatic hydrocarbons, preferably benzene, toluene, o-xylene, m-xylene, p-xylene; or corresponding mixtures thereof.

The term diastereomerically pure describes within the scope of the present invention compounds of formula (I), which are present in a diastereomeric purity of at least 85% de, preferably at least 90% de, particularly preferably >95% de. The term de (diastereomeric excess) is known in the art and describes the optical purity of diastereomeric compounds.

The term enantiomerically pure describes within the scope of the present invention compounds of formula (I), which are present in an enantiomerical purity of at least 85% ee, preferably at least 90% ee, particularly preferably >95% ee. The term ee (enantiomeric excess) is known in the art and describes the optical purity of chiral compounds.

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Preferred are alkyl groups with 1 to 4 carbon atoms, particularly preferably alkyl groups with 1 to 2 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{3-7}$-cycloalkyl" (including those which are part of other groups) are meant cyclic alkyl groups with 3 or 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy and fluorine.

By the term "aryl" (including those which are part of other groups) are meant aromatic ring systems with 6, 10 or 14 carbon atoms. Examples include: phenyl, naphthyl, anthracenyl or phenanthrenyl, the preferred aryl group being phenyl.

"Halogen" within the scope of the present invention denotes fluorine, chlorine, bromine or iodine. Unless stated to the contrary, fluorine, chlorine and bromine are regarded as preferred halogens.

Methods of Preparation

The following methods are suitable, for example, for preparing compounds of general formula (I):

a) reacting a compound of general formula

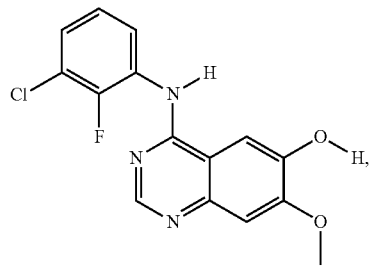

(II)

with a compound of general formula

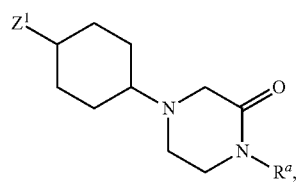

(III)

wherein
$R^a$ is as hereinbefore defined and $Z^1$ denotes a leaving group such as a halogen atom, e.g. a chlorine or bromine atom, a sulphonyloxy group such as a methanesulphonyloxy or p-toluenesulphonyloxy group or a hydroxy group.

With a compound of general formula (III), wherein $Z^1$ denotes a halogen atom or a sulphonyloxy group, the reaction is expediently carried out in a solvent such as ethanol, isopropanol, acetonitrile, toluene, tetrahydrofuran, dioxane, dimethylformamide, dimethylsulphoxide or N-methylpyrrolidinone, preferably in the presence of a base such as potassium carbonate, potassium-tert-butoxide, sodium hydride or N-ethyl-diisopropylamine, at temperatures in the range from 20° C. to 160° C., for example at temperatures in the range from 60° C. to 140° C.

With a compound of general formula III wherein $Z^1$ denotes a hydroxy group, the reaction is carried out in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycol diethylether at temperatures between −50 and 150° C., but preferably at temperatures between −20 and 80° C.

b) reacting a compound of general formula (IV)

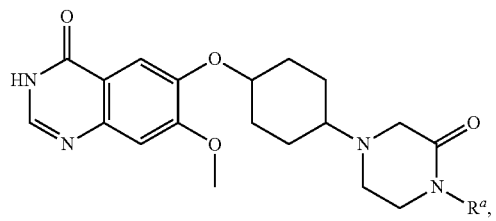

(IV)

wherein $R^a$ is as hereinbefore defined, with a halogenating agent, for example an acid halide such as thionyl chloride, thionyl bromide, phosphorus trichloride, phosphorus pentachloride, phosphorus oxychloride, or triphenylphosphine/carbon tetrachloride or triphenylphosphine/N-chlorosuccinimide to obtain an intermediate compound of general formula (V),

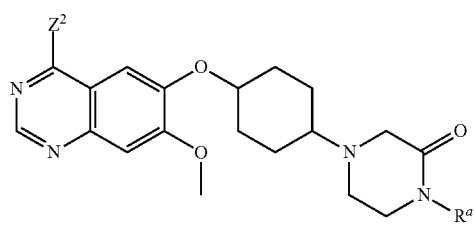

(V)

wherein $R^a$ is as hereinbefore defined and $Z^2$ denotes a halogen atom such as a chlorine or bromine atom, and subsequent reaction with a compound of general formula (VI),

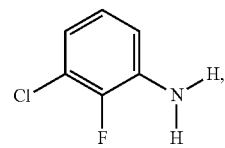

(VI)

or the salts thereof.

The reaction with the halogenating agent is optionally carried out in a solvent such as methylene chloride, chloroform, acetonitrile or toluene and optionally in the presence of a base such as N,N-diethylaniline, triethylamine or N-ethyl-diisopropylamine at temperatures in the range from 20° C. to 160° C., preferably from 40° C. to 120° C. Preferably, however, the reaction is carried out with thionyl chloride and catalytic amounts of dimethylformamide at the boiling temperature of the reaction mixture or with phosphorus oxychloride in acetonitrile in the presence of triethylamine at the boiling temperature of the reaction mixture or with triphenylphosphine/carbon tetrachloride or with triphenylphosphine/N-chlorosuccinimide in acetonitrile.

The reaction of the compound of general formula (VI) with the compound of general formula (VII) or the salts thereof is conveniently carried out in a solvent such as ethanol, isopropanol, acetonitrile, dioxane or dimethylformamide, optionally in the presence of a base such as potassium carbonate, triethylamine or N-ethyl-diisopropylamine, at temperatures in the range from 20° C. and 160° C., preferably from 60° C. to 120° C. However, the reaction is preferably carried out in isopropanol at the boiling temperature of the reaction mixture.

The reaction of a compound of general formula (V) to obtain a compound of general formula (I) may also be carried out as a one-pot reaction, for example in acetonitrile in the presence of triethylamine.

c) reacting a compound of general formula

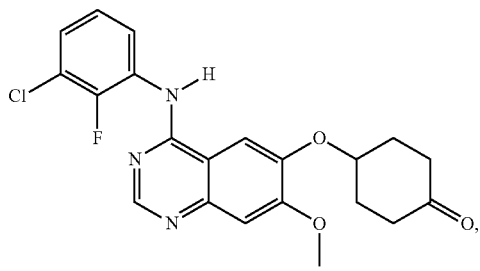

(VII)

with a compound of general formula

H—R$^a$, (VIII)

wherein
R$^a$ is as hereinbefore defined, in the presence of a reducing agent.

The reductive amination is carried out for example in a solvent such as dichloromethane, 1,2-dichloroethane, methanol, ethanol, tetrahydrofuran or dioxane in the presence of a reducing agent such as sodium triacetoxyborohydride or sodium cyanoborohydride, optionally in the presence of acetic acid at temperatures between 0° C. and 80° C. The reductive amination may also be carried out with hydrogen in the presence of a catalyst such as palladium on activated charcoal or platinum oxide. Another possibility is to form the enamine from the ketone of general formula VII and the amine of general formula VIII while cleaving hydrogen, for example with titanium (IV)-isopropoxide, and then to reduce this, for example with sodium borohydride or hydrogen/palladium on activated charcoal.

In the reactions described hereinbefore any reactive groups present such as hydroxy, amino, alkylamino or imino groups may be protected during the reaction by conventional protective groups which are cleaved again after the reaction.

For example a protecting group for a hydroxy group might be the trimethylsilyl, acetyl, trityl, benzyl or tetrahydropyranyl group.

Protecting groups for an amino, alkylamino or imino group might be, for example, the formyl, acetyl, trifluoroacetyl, ethoxycarbonyl, tert.-butoxycarbonyl, benzyloxycarbonyl, benzyl, methoxybenzyl or 2,4-dimethoxybenzyl group.

Any protective group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

A benzyl, methoxybenzyl or benzyloxycarbonyl group, however, is cleaved by hydrogenolysis, for example, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and under a hydrogen pressure of 1 to 7 bar, but preferably from 3 to 5 bar. A 2,4-dimethoxybenzyl group, however, is preferably cleaved in trifluoroacetic acid in the presence of anisole, thioanisole, pentamethylbenzene or triethylsilane.

A tert.-butyl or tert.-butyloxycarbonyl group is preferably cleaved by treatment with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treatment with an acid such as hydrochloric acid, optionally in the presence of a solvent such as acetic acid at temperatures between 50 and 120° C. or by treatment with sodium hydroxide solution, optionally in the presence of a solvent such as tetrahydrofuran at temperatures between 0 and 50° C.

Other suitable protective groups and possible ways of introducing and cleaving them are described for example in "Protective Groups in Organic Synthesis" by Theodora W. Greene and Peter G. M. Wuts, Wiley-VCH, or Philip Kocienski, Protecting Groups, 3rd ed. 2004, THIEME.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids or bases. Acids which may be used for this purpose include for example hydrochloric acid, hydrobromic acid, sulphuric acid, methanesulphonic acid, ethanesulphonic acid, benzenesulphonic acid, p-toluenesulphonic acid, phosphoric acid, fumaric acid, succinic acid, benzoic acid, salicylic acid, mandelic acid, lactic acid, malonic acid, citric acid, L-malic acid, L-tartaric acid or maleic acid. Suitable bases for this purpose include for example sodium hydroxide solution, potassium hydroxide solution, calcium hydroxide, diethanolamine or N-methyl-D-glucamine.

The compounds of general formulae II to VIII used as starting materials are known from the literature to some extent or may be obtained by methods known from the literature (cf. Examples I to IX), optionally with the additional introduction of protecting groups.

Standard processes for preparing the starting materials are described for example in "March's Advanced Organic Chemistry" by Michael B. Smith and Jerry March, Wiley-VCH or in "Science of Synthesis/Houben-Weyl" published by Thieme.

As already mentioned hereinbefore, the compounds of general formula (I) according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible to block the transmission of signals to components located further downstream.

The following Examples are intended to illustrate the present invention without restricting it:

Preparation of the Starting Compounds

Example I

4-[(3-chloro-2-fluoro-phenyl)amino]-6-(4-oxo-cyclohexyloxy)-7-methoxy-quinazoline

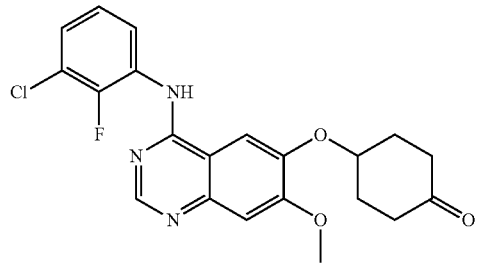 [SMILES: COc1cc2ncnc(Nc3cccc(Cl)c3F)c2cc1OC1CCC(=O)CC1]

25 ml of 4M sulphuric acid are added to 9.0 g 4-[(3-chloro-2-fluoro-phenyl)amino]-6-(1,4-dioxa-spiro[4.5]decan-8-yl-oxy)-7-methoxy-quinazoline in 110 ml of tetrahydrofuran and the mixture is stirred for 18 hours at ambient temperature. The mixture is made alkaline with 4M sodium hydroxide solution and extracted several times with ethyl acetate. Thecombined organic phases are dried, evaporated down and stirred with diethyl ether. The solid is suction filtered and dried.

Yield: 7.4 g (90% of theory)
Mass spectrum (ESI$^+$): m/z=416, 418[M+H]$^+$

Example II

4-[(3-chloro-2-fluoro-phenyl)amino]-6-(1,4-dioxa-spiro[4.5]decan-8-yl-oxy)-7-methoxy-quinazoline

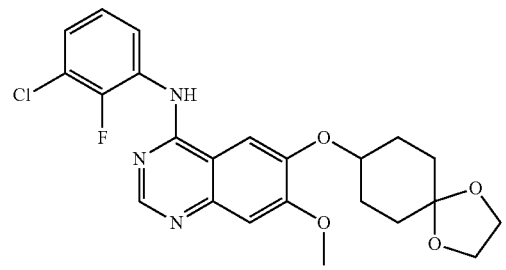 [SMILES: COc1cc2ncnc(Nc3cccc(Cl)c3F)c2cc1OC1CCC2(CC1)OCCO2]

12.5 g potassium carbonate and 16 g 8-methanesulphonyloxy-1,4-dioxa-spiro[4.5]decan (cf. for example Journal of Medicinal Chemistry (1992), 35(12), 2243-7) in 125 ml dimethylformamide are added at 50° C. to 18.1 g 4-[(3-chloro-2-fluoro-phenyl)amino]-6-hydroxy-7-methoxy-quinazoline (cf. for example Bioorganic & Medicinal Chemistry Letters (2006), 16(18), 4908-4912) and the mixture is stirred for 18 hours at 80° C. Another 4.7 g potassium carbonate and 4.0 g 8-methanesulphonyloxy-1,4-dioxa-spiro[4.5]decan are added and the mixture is stirred for a further 7 hours at 80° C. The reaction mixture is cooled, diluted with water and ethyl acetate and the precipitate formed is suction filtered and dried.

Yield: 12.2 g (47% of theory)
Mass spectrum (ESI$^+$): m/z=460, 462[M+H]$^+$

Example III

4-[(3-chloro-2-fluoro-phenyl)amino]-6-(4-oxo-cyclohexyloxy)-7-methoxy-quinazoline

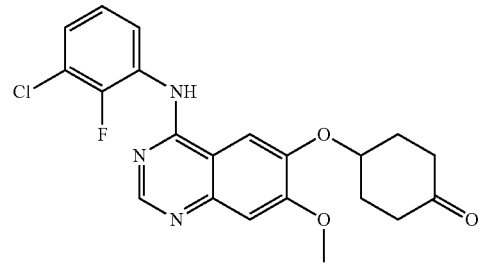 [SMILES: COc1cc2ncnc(Nc3cccc(Cl)c3F)c2cc1OC1CCC(=O)CC1]

8.5 ml phosphorus oxychloride are added dropwise to 17 g 3,4-dihydro-4-oxo-6-(1,4-dioxa-spiro[4.5]decan-8-yl-oxy)-7-methoxy-quinazoline in 120 ml acetonitrile and the mixture is heated to an internal temperature of 40° C. Then 13 ml triethylamine are added dropwise and the reaction mixture is refluxed for 2 hours. The mixture is cooled to ambient temperature, combined with 3.6 ml triethylamine and then 7.5 ml of 3-chloro-2-fluoro-5-aniline in 10 ml acetonitrile are added dropwise thereto. The reaction mixture is heated to 40° C. for 5 hours, then cooled and the precipitate is suction filtered. The solid is combined with a mixture of 1M hydrochloric acid and 6M isopropanolic hydrochloric acid and stirred for 24 hours. The precipitate is suction filtered, again combined with a mixture of 1M hydrochloric acid and 6M isopropanolic hydrochloric acid and stirred for 6 hours. The precipitate is suction filtered and divided between 1M sodium hydroxide solution and dichloromethane. The organic phase is separated off, dried and evaporated down.

Yield: 17 g (80% of theory)
Mass spectrum (ESI$^+$): m/z=416, 418[M+H]$^+$

Example IV 3,4-dihydro-4-oxo-6-(1,4-dioxa-spiro[4.5]decan-8-yl-oxy)-7-methoxy-quinazoline

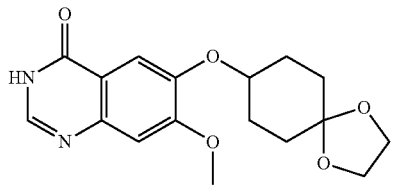 [SMILES: COc1cc2nc[nH]c(=O)c2cc1OC1CCC2(CC1)OCCO2]

16.0 g 3-benzyl-3,4-dihydro-4-oxo-6-(1,4-dioxa-spiro[4.5]decan-8-yl-oxy)-7-methoxy-quinazoline in 150 ml glacial acetic acid are hydrogenated in the presence of 1.6 g palladium on activated charcoal (10% Pd) at 60° C. at a hydrogen pressure of 50 psi. The catalyst is filtered off and the filtrate is evaporated down, combined with toluene and evaporated down again. The residue is mixed with water and made slightly alkaline with saturated sodium hydrogen carbonate solution. The precipitate is suction filtered and dried.

Mass spectrum (ESI$^+$): m/z=333[M+H]$^+$

Example V 3-benzyl-3,4-dihydro-4-oxo-6-(1,4-dioxa-spiro[4.5]decan-8-yl-oxy)-7-methoxy-quinazoline

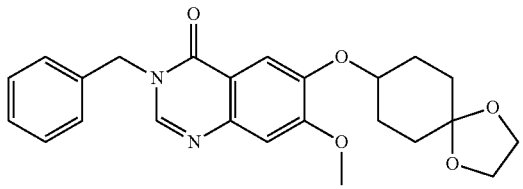 [SMILES: COc1cc2ncn(Cc3ccccc3)c(=O)c2cc1OC1CCC2(CC1)OCCO2]

16.0 g potassium carbonate and 20.0 g 8-methanesulphonyloxy-1,4-dioxa-spiro[4.5]decan are added at 50° C. to 20.0 g 3-benzyl-3,4-dihydro-4-oxo-6-hydroxy-7-methoxy-quinazoline in 150 ml N,N-dimethylformamide and the mixture is vigorously stirred for 18 hours at 80° C. To complete the reaction potassium carbonate and 8-methanesulphonyloxy-1,4-dioxa-spiro[4.5]decan are each added three times and in each case the mixture is stirred for several hours at 80° C. The reaction mixture is cooled and slowly combined with a total of 500 ml of water. The precipitate is suction filtered, washed with water and dried.

Mass spectrum (ESI$^+$): m/z=423[M+H]$^+$

Example VI 3-benzyl-3,4-dihydro-4-oxo-6-acetyloxy-7-methoxy-quinazoline

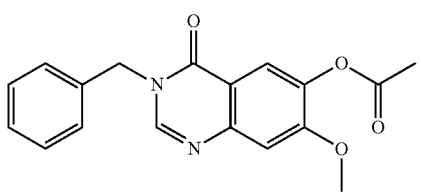 [SMILES: COc1cc2ncn(Cc3ccccc3)c(=O)c2cc1OC(C)=O]

169 g 3,4-dihydro-4-oxo-6-acetyloxy-7-methoxy-quinazoline, 118.8 ml benzylbromide and 138.2 g potassium carbonate are heated to 35-40° C. in 1600 ml acetone for 8 hours. The mixture is stirred for 15 hours at ambient temperature and then combined with 2000 ml of water. The suspension is cooled to 0° C., the precipitate is suction filtered, washed with 400 ml of water and 400 ml tert.-butylmethylether and dried at 50° C. The solid is dissolved in 4000 ml methylene chloride, filtered and evaporated down. The residue is suspended in tert.-butylmethylether, suction filtered and dried at 50° C. Yield: 203 g (86% of theory)

R$_f$ value: 0.80 (silica gel, methylene chloride/ethanol=9:1)

Mass spectrum (ESI$^+$): m/z=325[M+H]$^+$

Example VII 3-benzyl-3,4-dihydro-4-oxo-6-hydroxy-7-methoxy-quinazoline

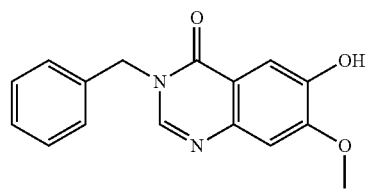 [SMILES: COc1cc2ncn(Cc3ccccc3)c(=O)c2cc1O]

Method A:

168.5 g 6-hydroxy-7-methoxy-benzo[d][1,3]oxazin-4-one are dissolved in 1200 ml of toluene and 74.7 ml benzylamine are added. The mixture is refluxed for 15 hours and then cooled to ambient temperature. The precipitate is filtered off and washed with tert.-butylmethylether.

Yield 124 g (72% of theory)

Method B:

200 g 3-benzyl-3,4-dihydro-4-oxo-6-acetyloxy-7-methoxy-quinazoline are suspended in 200 ml of water and 1000 ml of ethanol. 300 ml of 10N sodium hydroxide solution are added at ambient temperature and the mixture is heated to 30° C. for 1 hour. After the addition of 172 ml acetic acid and 2000 ml of water the mixture is stirred for 20 hours at ambient temperature. The precipitate is suction filtered, washed with water and acetone and dried at 60° C.

Yield: 172.2 g (98% of theory)

R$_f$ value: 0.25 (silica gel, methylene chloride/ethanol=19:1)

Mass spectrum (ESI$^+$): m/z=283[M+H]$^+$

Example VIII

6-Hydroxy-7-methoxy-benzo[d][1,3]oxazin-4-one

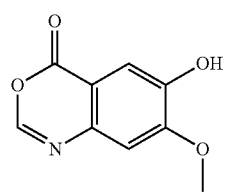

1 g 2-amino-5-hydroxy-4-methoxy-benzoic acid (prepared by reacting methyl2-nitro-4,5-dimethoxy-benzoate with potassium hydroxide solution to obtain the 2-nitro-5-hydroxy-4-methoxy-benzoic acid potassium salt and subsequent catalytic hydrogenation in the presence of palladium on activated charcoal) and 20 ml triethyl orthoformate are heated to 100° C. for 2.5 hours. After cooling to ambient temperature the precipitate is suction filtered and washed with diethyl ether.

Yield: 0.97 g (93% of theory)

$R_f$ value: 0.86 (silica gel, methylene chloride/methanol/acetic acid=90:10:1)

Mass spectrum (ESI$^+$): m/z=194[M+H]$^+$

Example IX 4-chloro-6-(1,4-dioxa-spiro[4.5]decan-8-yl-oxy)-7-methoxy-quinazoline

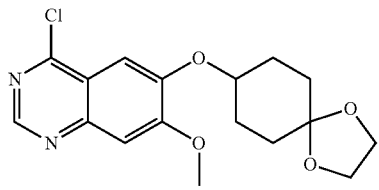 [SMILES: COc1cc2ncnc(Cl)c2cc1OC1CCC2(CC1)OCCO2]

6 ml phosphorus oxychloride are added dropwise to 12.1 g of 3,4-dihydro-4-oxo-6-(1,4-dioxa-spiro[4.5]decan-8-yl-oxy)-7-methoxy-quinazoline in 120 ml acetonitrile and the mixture is heated to an internal temperature of 40° C. Then 9.3 ml triethylamine are added dropwise and the reaction mixture is refluxed for 3 hours. The mixture is cooled to ambient temperature and left to stand overnight. The solution of the product is reacted further without purification (see Example III).

Preparation of the End Compounds

Example 1

4-[(3-chloro-2-fluoro-phenyl)amino]-6-[cis-4-(4-ethyl-3-oxo-piperazin-1-yl)-cyclohexyloxy]-7-methoxy-quinazoline and 4-[(3-chloro-2-fluoro-phenyl)amino]-6-[trans-4-(4-ethyl-3-oxo-piperazin-1-yl)-cyclohexyloxy]-7-methoxy-quinazoline

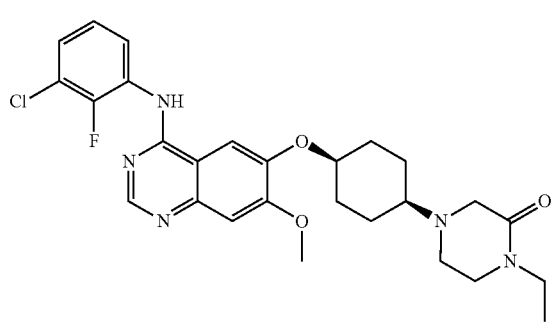

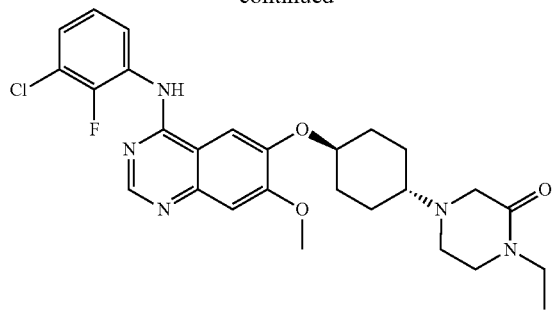

1500 mg of 4-[(3-chloro-2-fluoro-phenyl)amino]-6-(4-oxo-cyclohexyloxy)-7-methoxy-quinazoline in 50 ml dichloromethane are combined with 555 mg of 4-ethyl-3-oxo-piperazine and 250 µl of glacial acetic acid and stirred for 15 minutes at ambient temperature. Then 1100 mg of sodium triacetoxyborohydride are added and the mixture is stirred for 18 hours at ambient temperature. Some more sodium triacetoxyborohydride is added and the mixture is stirred for a further 3 hours. The reaction mixture is combined with dichloromethane and 1M sodium hydroxide solution, briefly stirred and extracted several times with dichloromethane. The combined organic phases are dried on magnesium sulphate and evaporated down. The two title compounds are obtained as a mixture by purification through a silica gel column with ethyl acetate/methanol/aqueous ammonia (95:5:0.1 to 80:20:0.1). The separation of the cis/trans mixture is carried out by preparative HPLC (xBridge™ C18 made by Waters; acetonitrile, water, aqueous ammonia). The isomers are assigned by 1H-NMR spectroscopy (400 MHz, dimethylsulphoxide-d6).

4-[(3-chloro-2-fluoro-phenyl)amino]-6-[cis-4-(4-ethyl-3-oxo-piperazin-1-yl)-cyclohexyloxy]-7-methoxy-quinazoline:
Yield: 610 mg (32% of theory)
Mass spectrum (ESI$^+$): m/z=528, 530[M+H]$^+$
characteristic signal at 4.71 (1H, m)

4-[(3-chloro-2-fluoro-phenyl)amino]-6-[trans-4-(4-ethyl-3-oxo-piperazin-1-yl)-cyclohexyloxy]-7-methoxy-quinazoline:
Yield: 520 mg (27% of theory)
Mass spectrum (ESI$^+$): m/z=528, 530[M+H]$^+$
characteristic signal at 4.45 (1H, m)

The following compounds are obtained analogously to Example 1:

(1) 4-[(3-chloro-2-fluoro-phenyl)amino]-6-[cis-4-(4-cyclopropylmethyl-3-oxo-piperazin-1-yl)-cyclohexyloxy]-7-methoxy-quinazoline and 4-[(3-chloro-2-fluoro-phenyl)amino]-6-[trans-4-(4-cyclopropylmethyl-3-oxo-piperazin-1-yl)-cyclohexyloxy]-7-methoxy-quinazoline

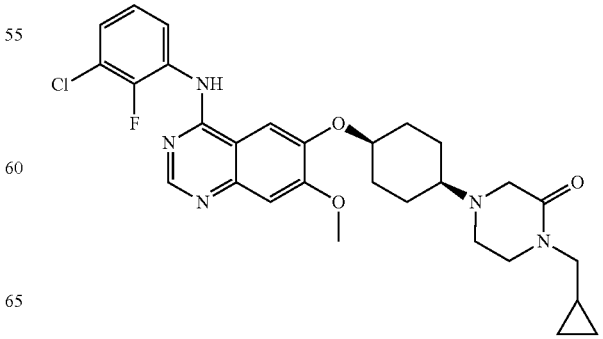

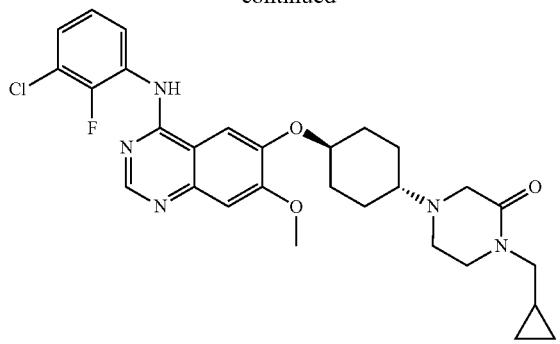

4-[(3-chloro-2-fluoro-phenyl)amino]-6-[cis-4-(4-cyclopropylmethyl-3-oxo-piperazin-1-yl)-cyclohexyloxy]-7-methoxy-quinazoline
Mass spectrum (ESI⁺): m/z=554, 556[M+H]⁺

4-[(3-chloro-2-fluoro-phenyl)amino]-6-[trans-4-(4-cyclopropylmethyl-3-oxo-piperazin-1-yl)-cyclohexyloxy]-7-methoxy-quinazoline
Mass spectrum (ESI⁺): m/z=554, 556[M+H]⁺

(2) 4-[(3-chloro-2-fluoro-phenyl)amino]-6-[cis-4-(4-butyl-3-oxo-piperazin-1-yl)-cyclohexyloxy]-7-methoxy-quinazoline and 4-[(3-chloro-2-fluoro-phenyl)amino]-6-[trans-4-(4-butyl-3-oxo-piperazin-1-yl)-cyclohexyloxy]-7-methoxy-quinazoline

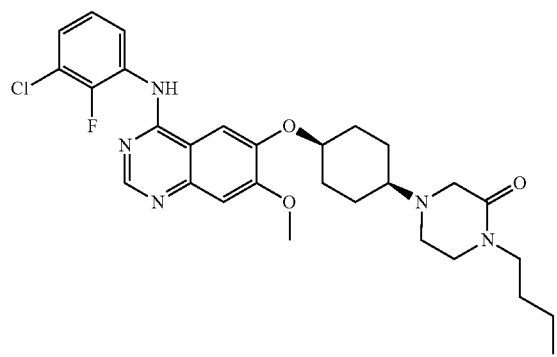

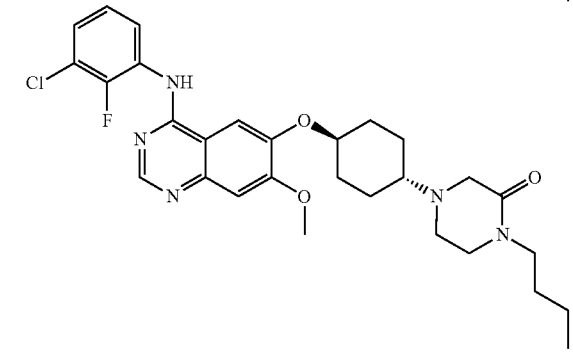

4-[(3-chloro-2-fluoro-phenyl)amino]-6-[cis-4-(4-butyl-3-oxo-piperazin-1-yl)-cyclohexyloxy]-7-methoxy-quinazoline
Mass spectrum (ESI⁺): m/z=556, 558[M+H]⁺

4-[(3-chloro-2-fluoro-phenyl)amino]-6-[trans-4-(4-butyl-3-oxo-piperazin-1-yl)-cyclohexyloxy]-7-methoxy-quinazoline
Mass spectrum (ESI⁺): m/z=556, 558[M+H]⁺

(3) 4-[(3-chloro-2-fluoro-phenyl)amino]-6-{cis-4-[4-(tetrahydropyran-4-yl)-3-oxo-piperazin-1-yl]-cyclohexyloxy}-7-methoxy-quinazoline and 4-[(3-chloro-2-fluoro-phenyl)amino]-6-{trans-4-[4-(tetrahydropyran-4-yl)-3-oxo-piperazin-1-yl]-cyclohexyloxy}-7-methoxy-quinazoline

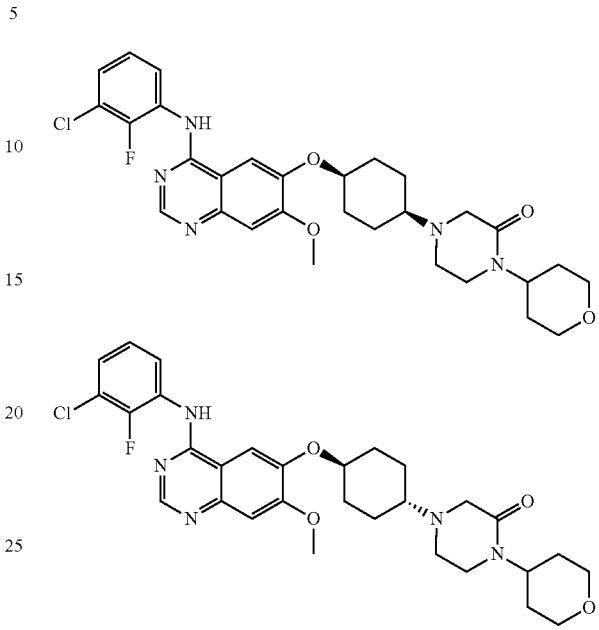

4-[(3-chloro-2-fluoro-phenyl)amino]-6-{cis-4-[4-(tetrahydropyran-4-yl)-3-oxo-piperazin-1-yl]-cyclohexyloxy}-7-methoxy-quinazoline
Mass spectrum (ESI⁺): m/z=584, 586[M+H]⁺

4-[(3-chloro-2-fluoro-phenyl)amino]-6-{trans-4-[4-(tetrahydropyran-4-yl)-3-oxo-piperazin-1-yl]-cyclohexyloxy}-7-methoxy-quinazoline
Mass spectrum (ESI⁺): m/z=584, 586[M+H]⁺

The following by-products were isolated during this reaction:

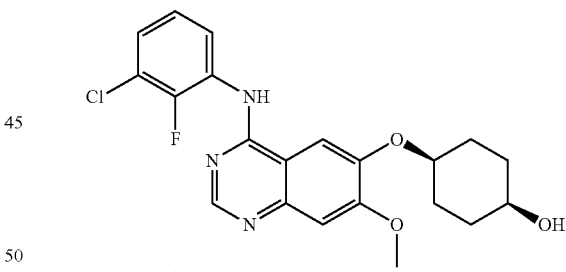

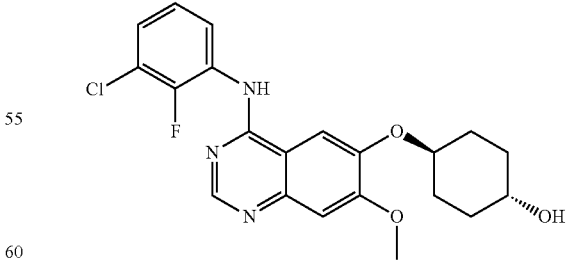

4-[(3-chloro-2-fluoro-phenyl)amino]-6-(cis-4-hydroxy-cyclohexyloxy)-7-methoxy-quinazoline
Mass spectrum (ESI⁺): m/z=418, 420[M+H]⁺

4-[(3-chloro-2-fluoro-phenyl)amino]-6-(trans-4-hydroxy-cyclohexyloxy)-7-methoxy-quinazoline
Mass spectrum (ESI⁺): m/z=418, 420[M+H]⁺

Biological Test

The biological properties of the new compounds are investigated as follows, for example:

The inhibition of the EGF-R-mediated signal transmission can be demonstrated e.g. with cells which express human EGF-R and whose survival and proliferation depend on stimulation by EGF or TGF-alpha. A murine haematopoietic cell line is genetically modified so as to express functional human EGF-R. The proliferation of this cell line can therefore be stimulated by EGF.

The test is carried out as follows:

The cells are cultivated in RPMI/1640 medium. The proliferation is stimulated with 20 ng/ml of human EGF (Promega). To investigate the inhibitory activity of the compounds according to the invention these compounds are dissolved in 100% dimethylsulphoxide (DMSO) and added to the cultures in various dilutions, the maximum DMSO concentration being 1%. The cultures are incubated for 48 hours at 37° C.

In order to determine the inhibitory activity of the compounds according to the invention the relative cell number is measured in O.D. units using the Cell Titer 96™ AQueous Non-Radioactive Cell Proliferation Assay (Promega). The relative cell number is calculated as a percentage of the control and the concentration of active substance which inhibits the proliferation of the cells by 50% (IC50) is derived therefrom.

The compounds of general formula (I) according to the invention exhibit IC50 values of <10 micromolar, preferably <1 micromolar, for example.

| Compound (Example No.) | Inhibition of EGFR-dependent proliferation $IC_{50}$ [nM] |
| --- | --- |
| 1, cis | 7.1 |
| 1, trans | 1.3 |
| 1(1), cis | 10.1 |
| 1(1), trans | 1.7 |
| 1(2), cis | 12.1 |
| 1(2), trans | 3.1 |
| 1(3), cis | 9.3 |
| 1(3), trans | 1.6 |

Indications

As has been found, the compounds of formula (I) are characterised in that by their versatility in the therapeutic field. Particular mention should be made of the possible applications for which the compounds of formula (I) according to the invention are preferably used on the basis of their pharmaceutical efficacy as tyrosine inhibitors.

The compounds of general formula (I) according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, the treatment of nasal polyps, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous, subcutaneous or intramuscular administration. For inhalation, according to the invention, solutions containing 0.01 to 1.0, preferably 0.1 to 0.5% active substance are suitable. For administration by inhalation the use of powders, ethanolic or aqueous solutions is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders.

Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

For pharmaceutical use the compounds according to the invention are generally used for warm-blooded vertebrates, particularly humans, in doses of 0.01-100 mg/kg of body weight, preferably 0.1-15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof to produce conventional galenic preparations such as plain or coated tablets, capsules, powders, suspensions, solutions, sprays or suppositories.

The Examples which follow illustrate the present invention without restricting its scope:

Examples of Pharmaceutical Formulations

A) Coated Tablets Containing 75 mg of Active Substance
Composition:

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl-pyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

B) Tablets Containing 100 mg of Active Substance
Composition:

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

C) Tablets Containing 150 mg of Active Substance

Composition:

| 1 tablet contains: | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

D) Hard Gelatine Capsules Containing 150 mg of Active Substance

Composition:

| 1 capsule contains: | |
| --- | --- |
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

E) Suppositories Containing 150 mg of Active Substance

Composition:

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

F) Suspension Containing 50 mg of Active Substance

Composition:

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

G) Ampoules Containing 10 mg Active Substance

Composition:

| active substance | 10.0 mg |
| --- | --- |
| 0.01N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

H) Ampoules Containing 50 mg of Active Substance

Composition:

| active substance | 50.0 mg |
| --- | --- |
| 0.01N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

I) Capsules for Powder Inhalation Containing 5 mg of Active Substance

| 1 capsule contains: | |
| --- | --- |
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg size of capsule: 3

J) Solution for Inhalation for Hand-Held Nebulisers Containing 2.5 mg Active Substance

| 1 spray contains: | |
| --- | --- |
| active substance | 2.500 mg |
| benzalkonium chloride | 0.001 mg |
| 1N hydrochloric acid | q.s. |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).
Contents of the container: 4.5 g

The invention claimed is:

1. A compound of formula (I)

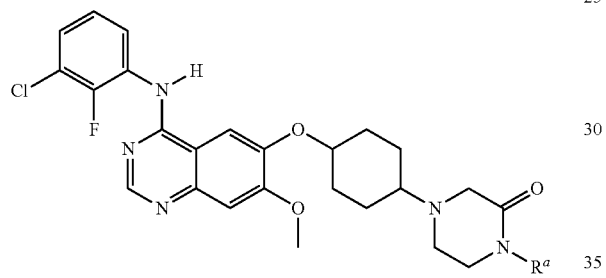

(I)

wherein:

$R^a$ denotes an ethyl, propyl, butyl, cyclopropyl, cyclopropylmethyl, cyclobutyl, cyclobutylmethyl, 3-tetrahydrofuranyl, tetrahydrofuranylmethyl, 3-tetrahydropyranyl, 4-tetrahydropyranyl- and tetrahydropyranylmethyl group, and wherein, unless stated otherwise, the above-mentioned alkyl groups may be straight-chain or branched, optionally in the form of the tautomers, the racemates, the enantiomers, the diastereomers and the mixtures thereof, and optionally the pharmacologically acceptable acid addition salts thereof.

2. The compound according to claim 1, wherein:

$R^a$ denotes a group selected from among ethyl, butyl, cyclopropylmethyl and 4-tetrahydropyranyl group, optionally in the form of the tautomers, the racemates, the enantiomers, the diastereomers and the mixtures thereof, and optionally the pharmacologically acceptable acid addition salts thereof.

3. A pharmaceutical formulation containing a compound of formula (I) according to claim 1.

4. An orally administered pharmaceutical formulation according to claim 3 containing a compound of formula (I) according to claim 1.

* * * * *